United States Patent [19]

Carter

[11] Patent Number: 4,963,532
[45] Date of Patent: * Oct. 16, 1990

[54] DSRNA-BASED PREVENTION OF VIRAL ESCAPE

[75] Inventor: William A. Carter, Birchrunville, Pa.

[73] Assignee: HEM Research, Inc., Rockville, Md.

[*] Notice: The portion of the term of this patent subsequent to Jan. 3, 2006 has been disclaimed.

[21] Appl. No.: 242,341

[22] Filed: Sep. 9, 1988

Related U.S. Application Data

[63] Continuation-in-part of Ser. No. 125,098, Nov. 25, 1987, abandoned.

[51] Int. Cl.$^5$ .............................................. A61K 31/70
[52] U.S. Cl. .................................... 514/44; 514/885; 514/934
[58] Field of Search .......................... 514/44, 885, 934

[56] References Cited

U.S. PATENT DOCUMENTS 4,795,744  1/1989  Carter .................................... 514/44

FOREIGN PATENT DOCUMENTS 0213921  3/1987  European Pat. Off. .

Primary Examiner—John W. Rollins
Attorney, Agent, or Firm—Nixon & Vanderhye

[57] ABSTRACT dsRNA reduces the phenomenon of viral escape and cellular damage attendant thereto. Viral escape is a process by which a virus of intracellular pathogen alters its host range or indirectly alters its susceptibility to antiviral or immunological therapies. Viruses do so by causing specific changes in their genomic/antigenic composition and/or by causing the elaboration of factors which enhance destructiveness of cells and their ability to multiply progeny virus. Animals susceptible to viral infections and pathology secondary to antigenic drift may have damage reduced by exposing them to dsRNA which prevents or substantially minimizes viral escape brought about through these mechanisms of molecular rearrangement and/or elaboration of factors which break down the natural host defenses.

11 Claims, 3 Drawing Sheets

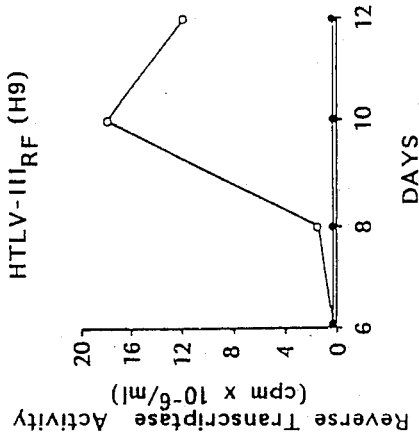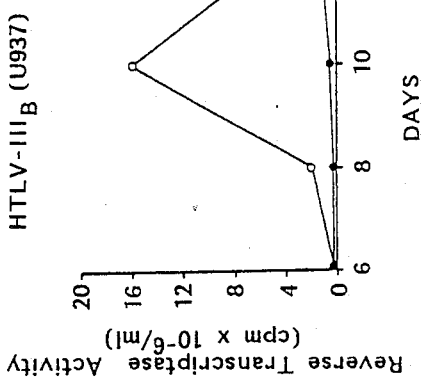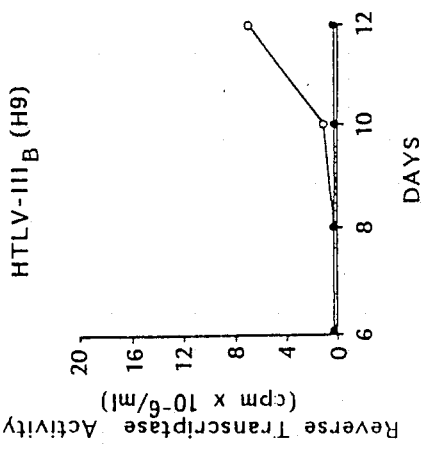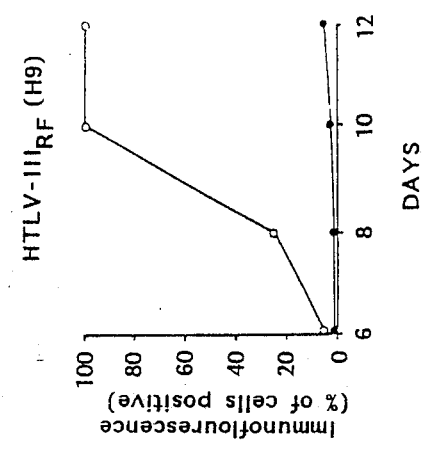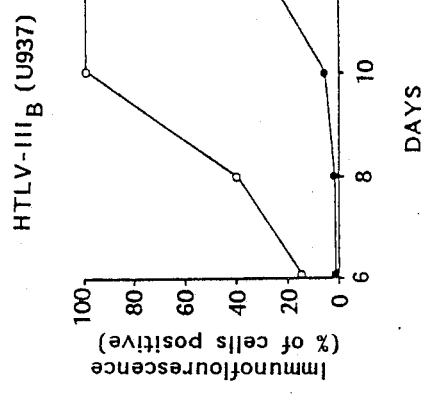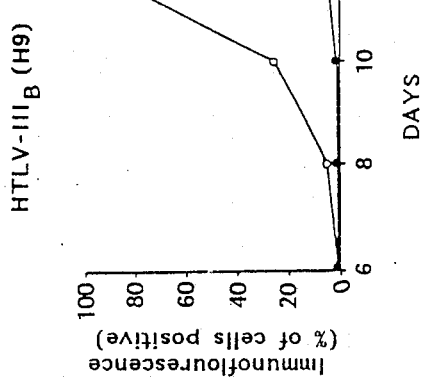

DSRNA-BASED PREVENTION OF VIRAL ESCAPE

This application is a continuation-in-part of application Ser. No. 125,098 filed Nov. 25, 1987 now abandoned. The use of dsRNA to prevent the biologic sequalae resulting from the phenomenon of viral escape, a process by which a virus alters its host range or indirectly alters its susceptibility to antiviral or immunologic therapies is described.

BACKGROUND OF THE INVENTION

Antigenic drift is a change in structure of a virus, such as the internal proteins, glycoproteins, glycolipids, etc., due to fundamental change in the genomic content of the virus particle. The genome may be comprised of either RNA molecules, e.g., herpes virus type 1 or type 2, etc. Variable host cell range, diseases morbidity, and the like, are the inevitable sequence of fundamental structural changes in the compositions of given groups of viral particles.

Human immunodeficiency virus (HIV), the etiologic agent of acquired immunodeficiency syndrome (AIDS), selectively infects and destroys the host's helper subset of T-lymphocytes thereby giving rise to severe opportunistic infections and certain neoplasias (1). Monocytes have also been identified as a major target for HIV infection and may be responsible for the frequent acute encephalopathy associated with AIDS (2). A comparison of various HIV isolates has revealed a high degree of genomic diversity. Whereas isolates such as HTLV-III$_8$ and LAV differ by less than 2%, the Haitian isolate HTLV-III$_{RF}$ shows much greater divergence (3). The most variable region of the HIV genome is the envelope (env) gene and variability in this region is a mechanism for escaping the host's immune response (4). However, this variation and variation that occurs throughout the remainder of the genome also reflects a potential for different efficacies of antiviral drugs against the many variants of HIV. Therefore, to be usefully predictive, anti-HIV drug testing must include diverse HIV isolates. In addition, potentially useful anti-HIV drugs can be screened for activity on monocytes as well as helper T lymphocytes since both lineages serve as major targets for human viruses in general and since both play a role in the pathogenesis of subacute/chronic infection in vivo. HIV-2 (also called LAV-2) has approximately only 60% homology with (or similarity to) HIV-1 has diverged from a common ancestor at an indeterminate past time.

Double-stranded RNAs (dsRNAs) are potent biological response modifiers having pleiotropic activities which include induction of the interferons (IFNs), activation of certain IFN-induced enzymes such as 2-5A synthetase, augmentation of natural killer and monocyte activities, and B and T cell mitogenic activities. Indeed, I have shown synthetic mismatched dsRNA of the form r(I)$_n$·r(C$_{12}$-U)$_n$ (Ampligen, a trademark of HEM Research, Inc., Rockville, Md., U.S.A.) to have anti-HIV activity in vitro; see my published European patent application No. 0,213,921. Furthermore, Ampligen and azidothymidine (AZT) acted synergistically against HIV in similar infection assays; see my copending application Ser. No. 07/028,823. As there described, in a clinical trial, I demonstrated that Ampligen improved the clinical status of ten patients with AIDS-related complex (ARC), lymphadenopathy syndrome (LAS) or AIDS while producing only rare, mild side effects.

In a continuing effort to characterize the full potential efficacy of dsRNAs and related mismatched dsRNAs in the treatment of HIV infection, I have extended by previous investigations to include the highly divergent HIV isolate HTLV-III$_{RF}$ (5) and three additional target cell lines, including the T-lymphoblastoid cell line H9 (6), the MTLV-I-transformed T cell line MT-2 (7), and the monocyte/macrophage cell line U937 (8). From these studies, I have concluded that dsRNA under certain circumstances may prevent viral escape of HIV as a prototype virus. Perhaps more importantly, I have determined that dsRNA can continue to be effective in a milieu consisting of different genomic variants of animal viruses as well as in the presence of factors which promote viral escape, such as antibodies which actually enhance viral replication and, therefore, the potential for viral escape.

Retroviruses in general, and HIV in particular, give rise to antibody-dependent viral enhancing (ADE) factors produced by the host. Antibody-dependent enhancement of HIV infection considerably worsens the infection and accelerates the rate of patient decline. This ADE prevents the host's immune system from raising antibodies effective against the viral invader and must be adequately controlled for effective therapy. In that the presence of ADE, may prevent animals from forming adequate or effective antibodies against pathogenic agents, my invention is of critical value since by protecting the animal against the effects of ADE it allows for adequate levels of neutralizing antibody to be produced.

Like other retroviruses, HIV-1 is characterized by high antigenic variation and genomic heterogeneity. Antigenic drift and the resulting highly polymorphic variants of the virus enable it to escape the host's immune defense mechanisms and may aggravate and delay the development of an effective hetrovaccine.

The production of enhancing factors to HIV in immunized animals raises serious concern about the types of antibodies that could be elicited by vaccine approaches in man. Preliminary observations indicate that some isolates are more susceptible to enhancement than others. Such viruses could prove valuable for identifying the epitope(s) responsible for antibody-dependent enhancement that should be removed from vaccine preparations.

At least two components of human serum enhance human immunodeficiency virus type 1 (HIV-1) infection and mask HIV-1 neutralizing antibody activity; Robinson et al (Lancet, Apr. 9, 1988, p. 790). The first is heat-stable, unique to HIV-1 seropositive sera, and is removed by protein-A chromatography. The second is heat-labile and ubiquitous; it is found in normal serum and is removed by heating at 60° C. for 1 hour or by treatment with cobra venom anticomplementary protein. Additionally, complement component C3 deficient serum lacks the labile activity although Clq deficient serum contains the labile factor. The data suggest that the two components are antibody and the alternative pathway of complement fixation. The mechanism of action does not involve an increase in either complement-mediated cytolosis or syncytium formation. The activity has been identified in the majority of patients tested to date.

Antibody-dependent enhancement (ADE) of human immunodeficiency virus type 1 (HIV-1) infection in vitro has been described recently and shown to require participation of the alternative pathway of complement or to involve an Fc receptor-mediated mechanism. Complement-mediated ADE results in an accelerated cytopathic effect in target cells which can abrogate the protective properties of neutralizing antibodies (Robinson et al, Lancet i:693–699, 1987; Robinson et al, Lancet i:790–795, 1988). This study utilized MT-2 cell cultures to demonstrate that ADE of HIV-1 infection causes an acceleration of several parameters indicative of HIV-1 infection including: HIV-1 antigen synthesis as detected by indirect immunofluorescence, mRNA accumulation as measured by a solution hybridization protocol, reverse transcriptase release, and progeny virus production. Thus, ADE of HIV-1 infection in vitro was characterized by an authentic, accelerated rate of HIV-1 infection.

Despite the presence of antibodies which neutralize the human immunodeficiency virus (HIV-1) in vitro, such antibodies fail to protect the infected individual from the immunological sequelae that lead to the Acquired Immune Deficiency Syndrome (AIDS) and, ultimately, to death. Recently, Robinson et al reported the existence of an immunoglobulin in the serum of greater than 60% of HIV-1 seropositive individuals that, in combination with the alternative pathway of complement, can lead to a more rapid viral-induced cytopathic effect. They demonstrated that the cytopathic effect (CPE) observed in this antibody-dependent enhancement of HIV-1 infection is the direct result of a more rapid infection of the target cell line by the HIV-1. This ADE of HIV-1 infection is manifested by more rapid accumulation of HIV-1-specific RNA as well as faster expression of detectable viral proteins and accelerated production of infectious virus particles. A majority of HIV patients have been observed to have this antibody-dependent enhancement. It is believed that a majority of other viruses, such as influenza, Dengue fever and related encephalitis, that exhibit antigenic drift and/or infectious, viral escape mediated through ADE or similar mechanisms exhibit similar factors.

ADE (source being Serum designated #110) was obtained from an anonymous donor confirmed to be HIV antibody positive by immunofluorescence and Western Blot (DuPont, Wilmington, Del.). The ADE serum was heat-inactivated for one-half hour at 60° C. then diluted 1:5 into growth medium prior to being assayed for ADE of HIV-1 infection. ADE accelerated cytopathic effect of HIV-1 as determined by a decrease in percent viable cells relative to control infection in the presence of Serum #110 and human complement serum. At high antibody concentration (1:20 dilution), less than 20% of MT-2 cells were viable compared to 100% cell viability in the presence of an equivalent dose of HIV-1 and 1:20 human complement serum. This enhancement of viral cytopathic effect extended to a dilution of 14,860 where MT-2 cell viability was reduced by 30%.

Phase contrast microscopy revealed that the decreased cell viability in the presence of enhancing serum and HIV-1 was accompanied by increased giant cell formation. I showed that ADE of HIV-1 infection was responsible not only for accelerated CPE but also for an accelerated progression of other parameters of HIV-1 infection including viral antigen and RNA synthesis, progeny virus production, and reverse transcriptase (RT) release.

Experiments were performed by culturing cells from the CD4+ cell line, MT-2, in the presence of HIV-1 alone, HIV-1 and human complement serum (1:20), HIV-1 and an enhancing serum plus 1:20 human complement serum, or virus-free H9 medium and enhancing serum plus 1:20 human complement serum. CD4+ cells are those cells which react (positively) to the monoclonal antibody CD4 which reacts with a specific subset of thymus-derived lymphocytes designated T4 of T helper cells. Twelve hours after challenge, cells were washed then resuspended in growth medium without added serum or virus. Cell suspensions were removed at 24, 48, 60 and 72 hours post-infection. The culture supernatants were assayed for infections virus and RT activity while the cells were assayed for HIV-1-specific antigen and HIV-1-specific RNA.

The rate of accumulation of viral antigen positive cells was increased in those cells challenged by HIV-1 in the presence of enhancing serum. For example, 48 hours post-challenge, 95% of MT-2 cells were expressing viral antigens by indirect immunofluorescence compared to only 15% and 10% of cells challenged by HIV-1 and complement of HIV-1 alone, respectively. Mock-infected cells did not express HIV-1 antigens. Therefore, ADE of HIV-1 infection was characterized by a decrease in time to detectable viral antigen synthesis.

I also observed that increases in HIV-1-specific RNA occurred sooner in cells exposed to enhancing antibody than in cells exposed to HIV-1 alone or HIV-1 and complement. Maximum quantities of HIV-1 a specific RNA for the latter two samples were never as high as the corresponding cells infected by HIV-1 in the presence of enhancing antibody. For example, at 60 hours, the cpm of hybridized probe to RNA from target cells in the ADE culture was 3631 compared to 347 for the HIV-1 alone and 374 for the HIV-1 and complement culture. It should be noted that maximum CPE in the ADE culture occurred after 60 hours so that the number of cells at the 72 hour time point was smaller than in other cultures or at other time points. The decrease in viable cell number was reflected by a decrease in HIV-1 RNA after 72 hours compared to 60 hours in the ADE culture.

If enhancing serum causes HIV-1-specific RNA and antigen to appear sooner, then one would expect increased infectious virus yields sooner, also. Infectious virus yields obtained from culture supernatants of cells infected in the presence of HIV-1 alone, HIV-1 and complement, and HIV-1 and enhancing serum with complement were evaluated.

From 24 hours after virus challenge to the endpoint at 72 hours, infectious virus yields were many times greater in cultures challenged in the presence of enhancing serum plus complement and HIV-1. At 72 hours, the infectious particles per milliliter obtained from the ADE culture were $1.3 \times 10^6$ compared to $1.2 \times 10^5$ for HIV-1 alone and $1.6 \times 10^5$ from the HIV-1 plus complement culture. These data demonstrate that ADE caused in accelerated appearance of and increase in infectious virus output from the target cells.

As a final measure of virus production, culture supernatants were assayed for reverse transcriptase released from the infected cells. Again, the ADE culture exhibited the earliest release of RT activity from the infected MT-2 cells. Detectable RT activity was present as early as 24 hours post-virus challenge with a maximum achieved at the endpoint of the assay, 72 hours. At 72 hours, the RT activity in supernatants from the ADE culture was $3.3 \times 10^6$ cpm/ml while the cells exposed to HIV-1 alone generated only $8.8 \times 10^5$ cpm/ml. Cells exposed to HIV-1 and complement were comparable to the latter cells generating $9.6 \times 10^5$ cpm/ml.

It should be noted that complement serum alone had the ability to activate HIV-1 virions in vitro. I have consistently observed minor decreases in time to HIV-1-specific CPE in the presence of normal human complement serum. The data support this finding since the MT-2 cells exposed to HIV-1 and complement exhibited a minor acceleration in synthesis of HIV-1 antigen, RT release, and infectious particles compared to cells exposed to HIV-1 alone. At early time points the same findings for HIV-1-specific RNA were observed although at 72 hours the cells challenged by HIV-1 alone demonstrated higher levels of RNA than the cells exposed to HIV-1 and complement serum. This was because the cells exposed to HIV-1 and complement serum had begun to exhibit lysis at that time while the cells exposed to HIV-1 alone had not.

Since virus, antibody, and complement were removed and the cells washed twelve hours after virus challenge, any effect that enhancing antibody and complement had on the virus must have occurred within the first twelve hours of virus exposure to the MT-2 cells. Even though both of the HIV-infected cultures without enhancing antibody (i.e., HIV-1 alone and HIV-1 plus complement serum) became 100% positive for HIV-1 antigen, they never came within a log of the RT activities or infectious virus released from the MT-2 cells exposed to virus in the presence of enhancing antibody.

Although not wishing to bound by any particular theory, these data can be interpreted to suggest that ADE not only increases the rate of detectable antigen expression in infected cells, but may also increase the copies of HIV-1 genome or mRNA in infected cells. This might occur either by an increase in the number of virions that infect each MT-2 cell or, alternatively, by an increase in transcriptional efficiency of the virus in the presence of enhancing serum. The latter seems unlikely since preliminary data suggests that antibodies conferring ADE of HIV-1 infection are directed toward the virus env gene products, gp41 and gp120.

In the detailed discussion of this invention (below), I demonstrate the effectiveness of dsRNA against various antigenic isolates of human retroviruses. I also show the ability of dsRNA to act in face of the above described antibody-dependent, complement- mediated enhancers of viral infection and viral escape.

Recent attempts to develop a vaccine to HIV have not been successful. All HIV-1 candidate vaccines tested in chimpanzees (animal models) to date have failed to afford protection from subsequent HIV-1 challenge. Recent reports describing antibody-dependent enhancement (ADE) of HIV-1 infection in vitro offer an intriguing possibility for vaccine failure in chimpanzees. Using an MT-2 cell assay for ADE, as described, it is demonstrated that complement-dependent enhancing antibodies are produced by chimpanzees infected by HIV-1. Further, HIV antibody-negative, fresh chimpanzee serum enhances HIV-1 infection. The data further suggest a complement-mediated ADE mechanism to explain the failure to passively immunize chimpanzees with human IgG fractions containing high HIV-1 neutralizing activity.

The majority of individuals infected with type-1 human immunodeficiency virus (HIV-1) exhibit antibodies which, in conjunction with the alternate complement pathway, accelerate HIV-1 infection of MT-2 target cells in vitro. This phenomenon, known as antibody-dependent enhancement (ADE), has been documented in other viral infectious processes (e.g., see Porterfield, *Adv. Virus Res.*, Vol. 31, p. 335, 1986 and Halstead, Science. Vol. 239, p. 476, 1988), and has been confirmed recently for complement-dependent ADE of HIV-1 infection in peripheral blood lymphocytes as well as extended to include an apparent Fc receptor-dependent mechanism for HIV-1 ADE. The Fc receptor-dependent mechanism was demonstrated not only in sera obtained from HIV-1 infected individuals, but from HIV-1-induced antisera obtained from guinea pigs and chimpanzees. Of special concern to vaccine development is the observation that complement-dependent ADE can reduce or completely abrogate the protective effects of neutralizing antibody within the same sera as well as between non-homologous human sera. The failure of candidate HIV-1 envelope vaccines to protect chimpanzees from infection despite the presence of neutralizing antibodies (see Berman, *Proc. Natl. Acad. Sci. U.S.A.*, Vol. 85, p. 5200, 1988) may be secondary to the concomitant induction of antibodies which promote ADE at the expense of neutralizing antibodies. Similarly, the failure to protect chimpanzees from HIV-1 infection by passive transfer of high titer human neutralizing immunoglobulin may be the result of ADE. Since the only surrogate animal available for HIV-1 infectivity studies is the chimpanzee, the demonstration of complement-dependent ADE in the chimpanzee is critical to the evaluation of candidate vaccines for the capacity to induce ADE. I have investigated by invention using HIV-1 induction of ADE in the chimpanzee and determined the comparative roles of chimpanzee versus human complement in mediation of the response by both seronegative and seropositive subjects.

Chimpanzees have been used as models for approximating human vaccine requirements. To investigate if antibody-negative chimpanzee serum could, indeed, cause an enhancement of HIV-1 infection, thereby leading to the high background CPE observed when chimpanzee serum is used as a source of complement, I performed two-fold dilutions of fresh, antibody-negative chimpanzee serum. I showed that human complement serum was capable of enhancing the infectivity of HIV-1 slightly but only to a dilution of 1:16; therefore, at a dilution of 1:20, no enhancement of infection could occur without the additional presence of antibody to HIV-1. Serum from a control chimpanzee X95 could cause an increased rate of viral-induced cytolysis to a dilution of 1:256 while serum from chimpanzee X35 could enhance infection to a dilution greater than 1:512. To determine if antibody-negative chimpanzee serum X35 was enhancing HIV-1 infection via complement-mediated mechanism, I tested the ability of cobra venom anticomplementary protein to abrogate the enhancing activity of the chimpanzee serum. I found that a one hour pre-incubation of chimpanzee serum with cobra venom factor completely inactivated serum X35, thus blocking the enhancement of HIV-1 infection in a manner analogous to ADE of HIV-1 infection by human serum. All further studies, therefore, utilized chimpanzee serum heat-inactivated one hour at 60° C. plus fresh human serum as a complement source. To confirm that increased CPE was associated with increased rate of HIV-1 infection, the effect of chimpanzee complement serum on accumulation of reverse transcriptase (RT) and immunofluorescence (IFA) was determined. Chimpanzee complement serum and chimpanzee complement serum plus serum from chimpanzee X91 greatly increased both RT activity and the percentage of IFA positive cells at 42 hours post virus challenge. Serum from chimpanzee X91 alone could not increase these parameters. Chimpanzee complement serum plus heat-inactivated serum X91 showed decreased RT activity compared to chimpanzee complement serum alone because X91 was neutralizing at this concentration (1:100). Human complement serum alone slightly increased both percent IFA positive cells and RT activity while this increase was greatly enhanced by the addition of heat-inactivated serum form chimpanzee X91. Thus, enhanced HIV-1 infection by chimpanzee complement serum as well as chimpanzee antibody and human complement serum were correlated with enhancement of CPE.

DESCRIPTION OF THE DRAWINGS

FIG. 1 consists of a series of six graphs, three showing reverse transcriptase activity and three showing immunofluorescence, demonstrating the antiviral activity of $rI_n \cdot r(C_{12},U)_n$, a prototype dsRNA, against the HIV isolates HTLV-III$_B$ and HTLV-III$_{RF}$ in the monocyte macrophage cell line U937. In this test cultures of U937 cells were preincubated in the presence and absence of $rI_n \cdot r(C_{12},U)_n$ (50 μg/ml) for 18 hours and then challenged with either HTLV-III$_B$ or HTLV-III$_{RF}$ as designated. The cell line used as a source of virus is shown in parenthesis. Equal portions of cultures were harvested for indirect immunofluoresence and reverse transcriptase assays at the days of incubation indicated. In these graphs, full circles are with $rI_n \cdot r(C_{12},U)_n$; open circles are without $rI_n \cdot r(C_{12},U)_n$.

Figure 2:
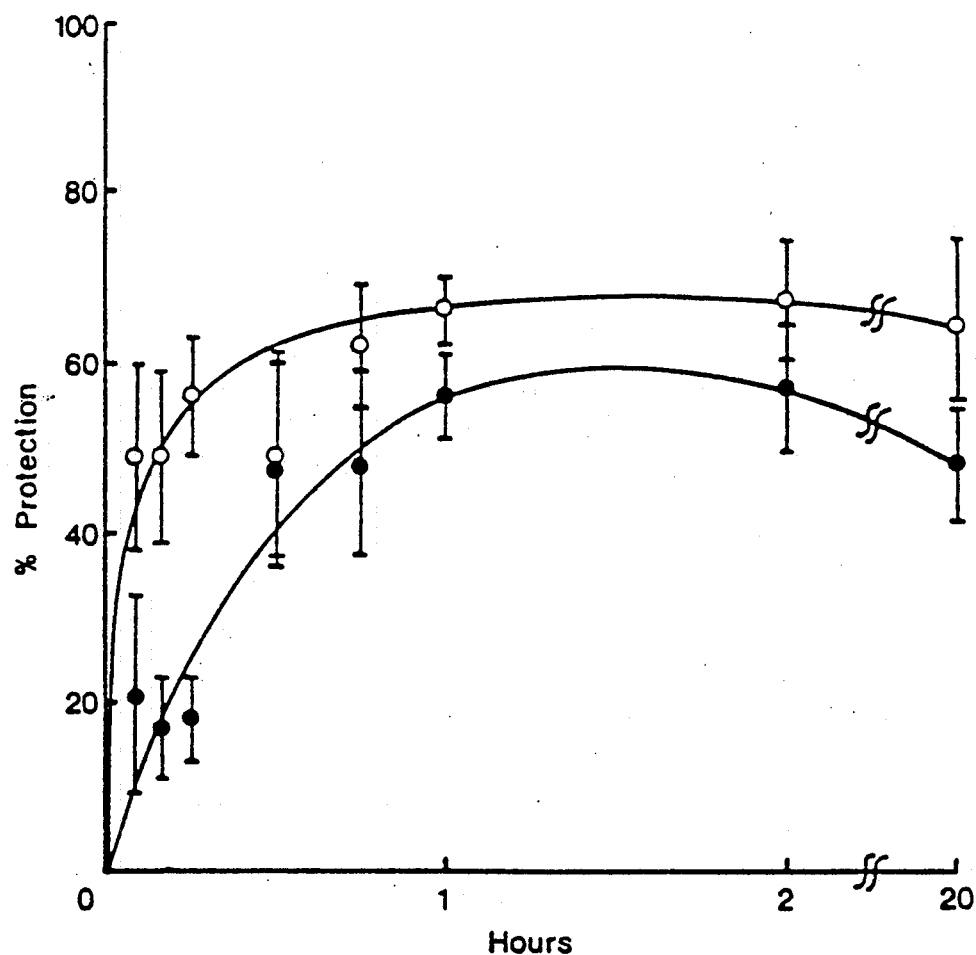
FIG. 2 illustrates the effect of various preincubation times in hours on $rI_n \cdot r(C_{12},U)_n$ anti-HIV activity reported as percent protection. Cultures of MT-2 cells (5×10$^5$ cell/ml) in 25 cm$^2$ culture flasks were preincubated with and without $rI_n \cdot r(C_{12},U)_n$ (50 μg/ml) for the various times indicated. Cells from one-half of each culture were then washed with RPMI-1640 to remove $rI_n \cdot r(C_{12},U)_n$ and suspended in an equal volume of growth medium devoid of $rI_n \cdot r(C_{12},U)_n$. The cells from each set of cultures were then challenged with HTLV-III$_B$(H9) at an m.o.i. of 1-5 in 96-well microtiter plates. Plates were assayed for cytopathic effect after 4 days of incubation and cytopathic effect after 4 days of incubation and infected controls in these experiments. In this graph open circles, as in FIG. 1, $rI_n \cdot r(C_{12},U)_n$ was present continuously; closed circles indicate $rI_n \cdot r(C_{12},U)_n$ was removed after the preincubation periods.
Figure 3:
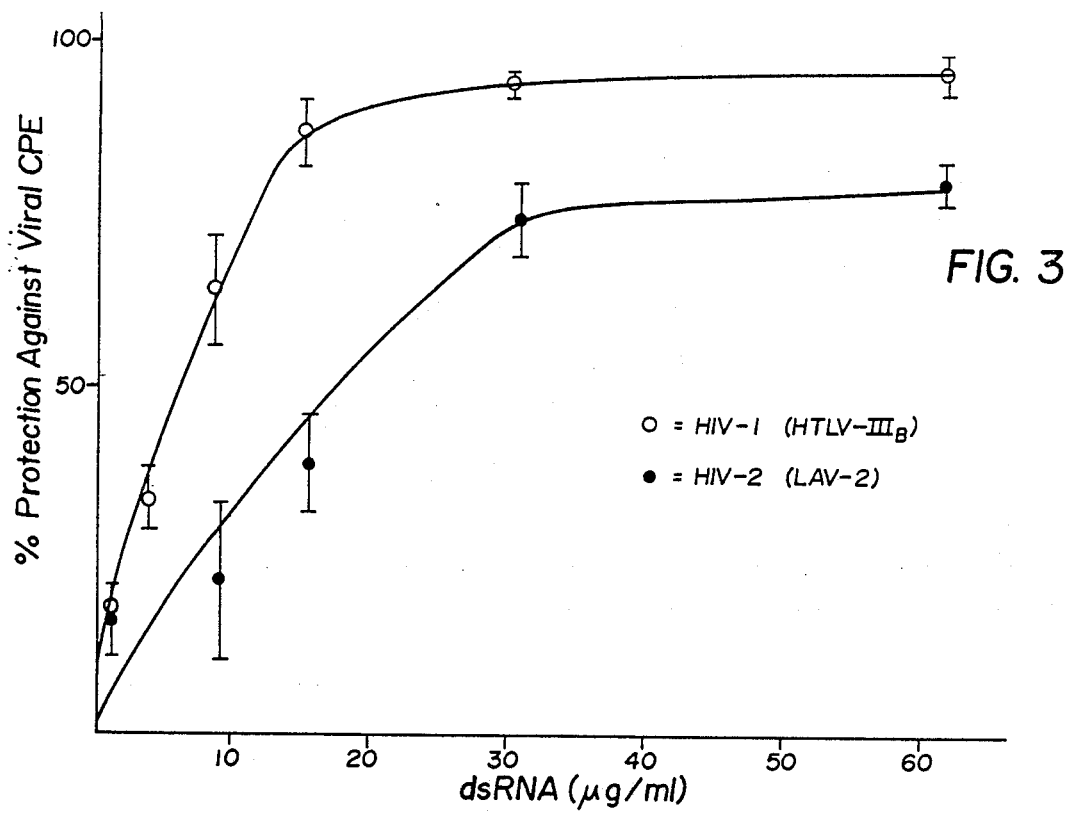
FIG. 3 is a graph plotting protection against viral CPE against quantity of dsRNA showing how dsRNA inhibits the multiplication and resultant CPE of animal viruses which have genomically or antigenically drifted from one another. The assay conditions are described in connection with FIGS. 1 and 2. As shown by these data, the dsRNA protects more than 90% against CPE from HIV-1 at approximately 60 μg/ml and approximately 75 to 80% protection against HIV-2 at the same dosage levels.
Figure 4:
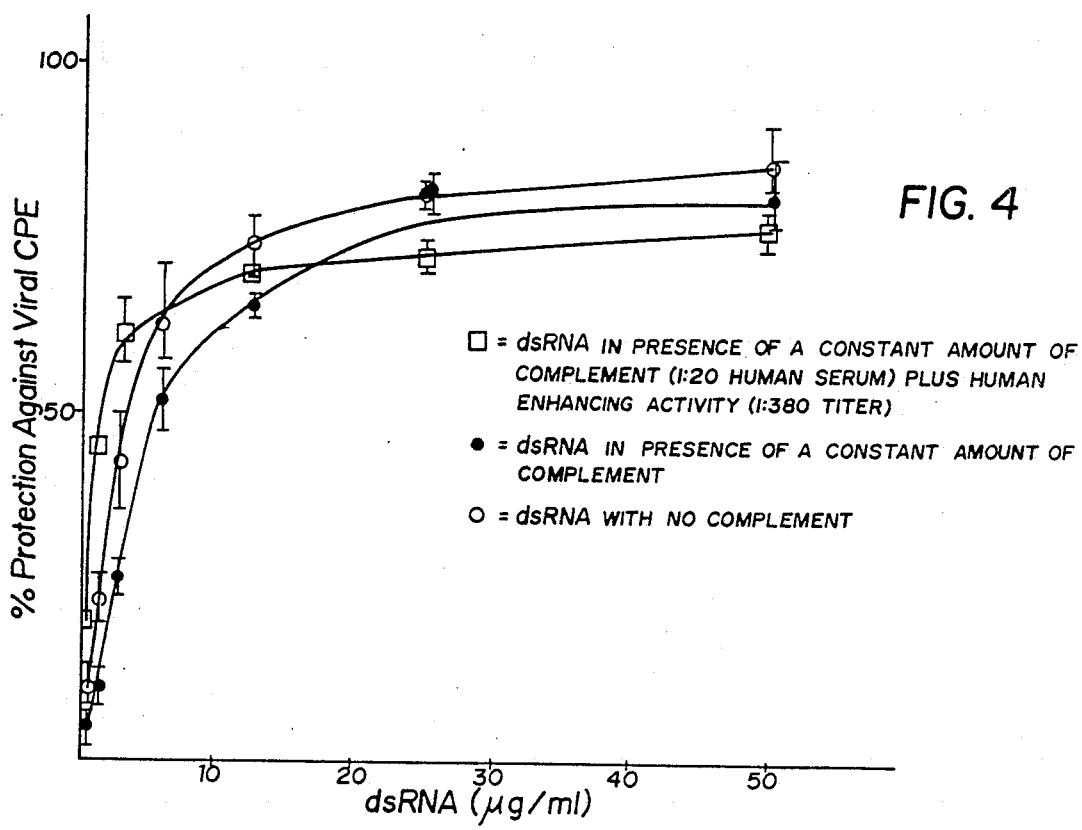
FIG. 4 also compares % protection against viral CPE with quantity of dsRNA. In this study dsRNA is shown to inhibit viral escape even in the presence of antibody dependent enhancers (ADE). These date show dsRNA protects against viral-induced CPE under these different experimental conditions: (a) in the presence of human enhancing activity plus complement (squares); (b) in the presence of complement without human enhancing activity (solid circles); and (c) in the absence of both complement and human enhancing activity.

In each of these Figures, the dsRNA used was $rI_n \cdot r(C_{12},U)_n$.

DETAILED DISCUSSION OF THE INVENTION

My invention includes methods of protecting animals, including humans, susceptible to viral infections against viral-induced pathology secondary to both antigenic drift (as evidenced by rearrangement of the viral particle structure) and genomic rearrangement as well. The animal to be protected, or cells isolated form the animal to be protected, are exposed to dsRNA which prevents or at least substantially minimizes viral escape secondary to molecular rearrangement in the viral particle structure. In the second stage of protection, the dsRNA counteracts or ameliorates the tissue pathology of viral particles which escape by virtue of genomic and/or antigenic rearrangements. In the third stage of protection, dsRNA provides a milieu for effective neutralizing antibody production by virtue of ability to counteract the effect of ADE factors and the like. Procedures of fixing and isolating the molecular arrangement of a viral particle structure while maintaining the particle's molecular arrangement within predetermined limits are also described.

Double-stranded RNA of the form $r(I)_n \cdot r(C_{12},U)_n$ (Ampligen) has been shown to be active against a prototypic chronic human pathogen, namely human immunodeficiency virus (HIV) using CEM and C3 cells as targets for infection by the highly similar HIV isolates HTLV-III$_B$ and LAV (9) and is the subject of my European patent application No. 0,213,921. The scope of Ampligen's anti-HIV activity is herewith examined in my present study using the highly-genetically divergent HIV isolate HTLV-III$_{RF}$, two additional target T-cell lines, H9 and MT-2, and a monocyte/macrophage cell line, U937. As judged by indirect immunofluorescence, reverse transcriptase activity and vital dye uptake, dsRNA is active against HTLV-III$_{RF}$ in H9, MT-2, C3 and U937 cells in addition to being active against HTLV-III$_B$ in U937 cells. A minimum of one hour preincubation of cells (MT-2) with Ampligen is required for maximum activity. This can be readily achieved in intravenous administration of a dose of dsRNA between approximately 50-1000 mg for a typical 60 kilogram individual. These results indicate that dsRNA's potential clinical efficacy will not be limited by the highly variable nature or host cell range of various animal viruses such as HIV, influenza, Dengue fever, etc., which properties have historically limited the utility of every other antiviral developed to date in the U.S. and abroad. The expression "highly variable nature" is an operational term embracing antigenic/genomic drift and/or production of factors such as ADE which allow viral particles to escape established immunosurveillant and control mechanisms.

Accordingly, I have now discovered a phenomenon of unexpected broad utility where by judicious use of dsRNA can prevent the common phenomenon of viral escape wherein by processes such as mutation or selection or antibody-dependent enhancing (ADE) factors, a virus over time alters its host range and/or expresses a variable nature which then alters its susceptibility to a given or specific antiviral and/or immunologic enhancing therapies, and/or protects itself against the emergence of bioactive neutralizing antibodies. The invention includes controlling the host's production of antibody-dependent enhancing factors or neutralizing the effects of such factors if produced.

The experiments described in detail below address whether or not viral genomic variation or host cell range will affect dsRNA's activity against viruses associated with "antigenic drift" and after subacute/chronic disease. These were important issues to address using human retroviruses since they demonstrate a potential maximum extreme of genomic variation (3) of virtually any human virus and since they can also infect cells of monocyte/macrophage lineage in addition to T-helper lymphocytes to provide a chronic nidus (sanctuary) which can shed virus indefinitely. Therefore, effective therapeutic intervention in this prototypic retroviral viral infection will imply broad applicability to other pathogenic viruses and intracellular pathogens with somewhat less antigenic drift or mutational abilities.

Unlike other modalities of treatment, realized or proposed, HIV genomic variation does not appear to be a major obstacle to dsRNA's antiviral activity since it was active against the diverse isolates HTLV-$III_B$ (which is actually a mixture of at least two similar variants) and HTLV-$III_{RF}$; supporting data are given in Table 1 and FIGS. 1-3, discussed below. I have shown dsRNA to be active against the French isolate, LAV. In addition, it is effective against HTLV-$III_B$ produced in two very different cell lines, H9 and U937 (FIG. 1), while I have also found it particularly effective against HTLV-$III_B$ produced in CEM and C3 cells and against LAV produced in H9, CEM and C3 cells. These latter results show a most startling and surprising lack of influence from variations in cell type, i.e., cell-specified modifications such as protein glycosylation, on dsRNA's anti-HIV activity.

I also examined dsRNA effectiveness in three different helper T-cell lines (C3, MT-2 and H9) and in a monocyte/macrophage cell line (U937). In addition to dsRNA activity against HTLV-$III_B$ in C3 cells and against LAV in C3 and CEM cells, reported earlier, I found it to be effective against HTLV-$III_{RF}$ in MT-2, H9 and U937 cells and against HTLV-$III_B$ in U937 cells; again see Table 1 and FIG. 1. Thus, the host cell range of any animal virus would not appear to be in obstacle to dsRNA's anti-viral activity. In light of recent evidence that cells of monocyte/macrophage lineage may be responsible for AIDS-associated encephalopathy, it was important to find that U937 cells were responsive to the anti-HIV activity of dsRNA.

Another aspect of this invention is the effect of various preincubation times on dsRNA's anti-viral activity. Previously, I allowed 1 8-24 hours of preincubation in anticipation of a need for IFN to be synthesized, secreted and accumulated in the medium before activity could be detected. However, now I report that full activity was observed in MT-2 cells with only brief periods (up to 60 minutes), while partial activity was observed with as little as 5 minutes preincubation prior to virus challenge; see FIG. 2.

By "mismatched dsRNAs" are meant those in which hydrogen bonding (base stacking) between the counterpart strands is relatively intact, i.e., is interrupted on average less than one base pair in every 29 consecutive base residues. The term "mismatched dsRNA" should be understood accordingly.

The dsRNA may be a complex of polyinosinate and a polycytidylate containing a proportion of uracil bases or guanidine bases, e.g., from 1 in 5 to 1 in 30 such bases (poly I · ($C_{4-29}$ × > U or G)).

The dsRNA may be of the general formula $rI_n \cdot (C_{11-14},U)_n$ or $rI_n \cdot (C_{12}U)_n$. The value of n is from 4 to 29. Other suitable examples of dsRNA are discussed below.

The mismatched dsRNAs preferred for use in the present invention are based on copolynucleotides selected from poly ($C_n$,G) in which n is an integer having a value of from 4 to 29, and are mismatched analogs of complexes of polyriboinosinic and polyribocytydilic acids, formed by modifying $rI_n \cdot rC_n$ to incorporate unpaired bases (uracil or guanidine) along the polyribocytidylate ($rC_n$) strand. Alternatively, the dsRNA may be derived from poly (I) · poly (C) dsRNA by modifying the ribosyl backbone of polyriboinosinic acid ($rI_n$) e.g., by including 2'-0-methyl ribosyl residues. These mismatched analogs of $rI_n \cdot rC_n$, preferred ones of which are of the general formula $rI_n \cdot r(C_{11-14},U)_n$ and $rI_n \cdot r(C_{29},G)_n$, are described by Carter and Ts'o in U.S. Pat. Nos. 4,130,641 and 4,024,222 the disclosures of which are hereby incorporated by reference. The dsRNAs described therein generally are suitable for use according to the present invention.

In the preferred mismatched dsRNA, $rI_n \cdot (C_{12},U)_n$, a region consisting of an uninterrupted stretch of 6 to 12 base pairs, i.e., one-half to one full turn of an RNA helix, serves both as a biotrigger causing release of lymphokines as an obligate intracellular co-factor for enzymes comprising the natural antiviral pathways. The mismatched regions consisting of uracil residues is periodically inserted in the polypyrimidine strand to accelerate dsRNA hydrolysis and thus prevent toxicity.

Other examples of mismatched dsRNA for use in the invention include:

poly (I)·poly ($C_4$,U)
poly (I)·poly ($C_7$,U)
poly (I)·poly ($C_{13}$,U)
poly (I)·poly ($C_{22}$,U)
poly (I)·poly ($C_{20}$,G)
poly (I)·poly ($C_{29}$,G) and
poly (I)·poly ($C_p$) 23 G>p The following studies describe dsRNA's ability to protect against antigenic and genomic drifts as well as ADEs and the resultant host cell range of properties of animal viruses. HIV, perhaps the virus with the most highly variable or host cell range, was selected as a prototypic virus for this study. The materials and methods use are described below.

Cells and Viruses—Cultures of H9, MT-2, U937, H9/HTLV-$III_B$, H9/HTLV-$III_{RF}$, U937/HTLV-$III_B$ and the HTLV-II-transformed T cell line C3 were grown and maintained at 37° C. in RPMI-1640 containing 16% heat-inactivated fetal bovine serum and 50 μg gentamycin/ml. Preparations of HTLV-$III_B$ and HTLV-$III_{RF}$ were obtained from conditioned H9/HTLV-$III_B$ H937/HTLV-$III_B$, or H9/HTLV-$III_{RF}$ culture fluids. HIV-2 (also called LAV-2) is well described in the recent medical literature. Conditioned culture fluids were clarified of cells by low speed centrifugation and 0.45 μm filtration. Media were replaced and cell densities reduced every two days in order to allow continual exponential cell multiplication.

In Vitro Infection Assays—Infection assays were performed either in 25 $cm^2$ flasks or in 96-well microtiter plates. For infection assays in flask cultures, target cells were challenged with HTLV-$III_B$ or HTLV-$III_{RF}$ at a multiplicity of infection (m.o.i.) of 1-5. Virus was allowed to adsorb for three hours and then removed by washing with RPMI-1640. Cultures were then incubated in 20 ml of fresh growth medium with or without dsRNAs, respectively, as before. Media were replaced and cell densities were equally reduced every two days. Samples for indirect immunofluorescence (IIF), reverse transcriptase (RT) activity and vital dye uptake were obtained at these times. IIF was performed with human anti-HIV p24 serum as described. RT activity in culture fluids was determined using poly(A)·(dT)$_{15}$ as template primer and 25 μCi [methyl-$^3$H] dTTP (80.1 Ci/mmol) per reaction. Vital dye uptake using Finter's neutral red was used as a measure of cytopathic effect.

Microtiter infection assays were performed in 96-well plates. Briefly, MT-2 cells were seeded at a density of $2 \times 10^5$ cells/0.2 ml/well and challenged with HIV at an m.o.i. of 1–5 (50 μl of conditioned H9/HTLV-III$_B$ culture fluid containing $2$–$10 \times 10^5$ infectious particles per well). Plates were incubated in modular incubator chambers flushed with 5% $CO_2$ in air and assayed for cytopathic effect after four days. Cytopathic effect was quantitated by vital dye (neutral red) uptake of poly-L-lysine adherent cells. Percent protection is defined as the percent of the range of A$_{540}$ values occurring between uninfected (cell control) and infected F(virus control) wells. Infectious viral titers were determined from 50% tissue culture infectious does (TCID$_{50}$) values obtained by endpoint microtitration on MT-2 cells in 96-well plates.

Results—The antiviral activity of dsRNA, a typical dsRNA, against the HIV isolate HTLV-III$_{RF}$ in C3, MT-2 and H9 target cells is shown in Table 1. Four days after viral challenge in C3 and MT-2 cells, and 6 days after viral challenge in H9 cells, in the absence of dsRNA, all cells were expressing HIV p24 antigen. This was associated with high levels of RT activity in culture fluids and dramatic reductions of viable cells. In contrast, with dsRNA present, very few cells were positive for HIV p24 expression, low or undetectable levels of RT activity were present, and there were no significant signs of cytopathic effect.

TABLE 1

| | Anti-HTLV-III$_{RF}$ Activity of Ampligen | | | |
|---|---|---|---|---|
| Cell Line* | Ampligen | Immuno-fluorescence (% Positive) | Neutral Red Uptake (A$_{540}$) | RT Activity (cpm × 10$^3$ml) |
| C3 | — | 100$^L$** | 0.07 | 2,369 |
| | + | 0.5 | 0.48 | 0 |
| MT-2 | — | 100$^L$ | 0.06 | 417 |
| | + | 2 | 0.70 | 10 |
| H9 | — | 100 | 0.30 | 1,823 |
| | + | 0.5 | 0.52 | 8 |

*Cells were preincubated in the presence and absence of Ampligen (50 μg/ml) for 18 hours prior to viral challenge. Cells preincubated with Ampligen were continued to be incubated with Ampligen in the growth medium following viral challenge.
**$^L$denotes extensive cytolysis The antiviral activity of dsRNA against the HIV isolates HTLV-III$_B$ and HTLV-III$_{RF}$ in U937 cells is shown in FIG. 1. Infection of U937 cells with HIV proceeds much slower than in C3, MT-2 and H9 cells. Therefore, samples of IIF and RT activity were obtained after 6, 8, 10 and 12 days of incubation. Also, HIV-induced cytopathic effect is mild in U937 cells; therefore, vital dye uptake was not used as a determinant for infection. In the absence of dsRNA, all cells were IFF positive for HIV p24 expression after 12 days for HTLV-III$_B$ produced in H9 cells. Also in the absence of dsRNA, HIV p24 expression was paralleled by a dramatic rise in RT activity. The decrease in RT activity which occurred after day 10 in U937 cultures infected with HTLV-III$_B$ (U937) or HTLV-III (H9) was due to a mild cytopathic effect which is observed early in infection. In striking contrast, the presence of dsRNA provided significant protection from an infection. This was evident after 12 days of incubation when fewer than 5% of cells challenged with HTLV-III$_B$ (Hg) or HTLV-III$_{RF}$ (H9) and fewer than 20% of cells challenged with HTLV-III$_B$ (U937) were positive for HIV p24 antigen expression. Furthermore, RT activities were greatly reduced or undetectable in all cultures infected in the presence of dsRNA. I have conducted similar experiments with other human retroviruses and developed identical conclusions. In addition, results with other RNAs showed the ubiquity of the phenomenon of sensitivity at the dosage range tested and independent of the antigenic qualities of the virus particle itself.

An analysis was made to determine the minimum length of time required for cells to be preincubated with dsRNA in order to achieve maximum antiviral activity. The results of this analysis, using MT-2 cells as targets and HTLV-III$_B$ (H9) as virus, are illustrated in FIG. 2. Here, one set of cultures was preincubated with dsRNA, then had dsRNA removed immediately following viral challenge so that antiviral activity would be a function of preincubation alone. A second set of cultures was preincubated with dsRNA and then continued to be incubated with dsRNA present following viral challenge. In both cases, antiviral activity was observed with as little as 5 minutes of preincubation for which 21% protection was provided by preincubation alone and 49% protection was provided by preincubation and continued incubation with dsRNA. Also in both cases, maximum antiviral activity was observed with a one hour preincubation period.

In conclusion, I have uncovered new evidence that dsRNA's antiviral activity is not limited by the highly mutable nature or host cell range of the pathogen virus or intracellular parasite operating alone or in concert with other (antigenically and/or genomically different) human viruses. This was indicated by dsRNA's activity against the divergent HIV isolates HTLV-III$_B$ and HTLV-III$_{RF}$, and ability to establish an antiviral state in three different helper T-cell lines (C3, MT-2 and H9) and in a monocyte/macrophage cell line. Furthermore, as little as 5–60 minutes preincubation with dsRNA was required for full anti-viral activity in vitro as opposed to conventional wisdom indicating that 8–24 hours pretreatment may be necessary. The spectrum of effectiveness against a highly mutagenic viruses (and/or against those associated with production of ADE to increase their latent pathogenicity) observed for dsRNAs in these in vitro studies is a clear indication of dsRNA's clinical effectiveness in the treatment of many human viral infections, especially those whose pathogenesis is associated with a subacute or chronic nature.

Table of References

1. Klatzmann, D., Barre-Sinoussi, F., Nugeyre, M.T., Gauguet, C., Vilmer, E., Griscelli, C., Brun-Vezinet, F., Rouzioux, C., Gluckman, J. C., Chermann, J. C., and Montagnier, L. 1984. Selective Tropism of Lymphadenopathy Associated Virus (LAV) for Helper Inducer T-lymphocytes. Science 225,59–63

2. Koenig, S., Gendelman, H. E. M Orenstein, J. M., DalCanto, M. C., Pezeshkpour, G. H., Yungbluth, M., Janotta, F., Aksamit, A., Martin, M. A. and Fauci, A. S. 1986. Detection of AIDS Virus in Macrophages in Brain Tissue from AIDS Patients with Encephalopathy. Science 233,1089–1093.

3. Hahn, B. H., Gonda, M. A., Shaw, G. M., Popovic, M., Hosie, J. A., Gallo, R. C. and Wong-Stall, F. 1985. Genomic Diversity of the Acquired Immune Deficiency Syndrome virus HTLV-III: Different Viruses Exhibit Greatest Divergence in Their Envelope Genes. Proc. Natl. Acad. Sci. (U.S.A.) 82,4813–4817.

4. Shaw, G. M., Hahn, B. H., Arya, S. K., Groopman, J. E., Gallo, R. C., and Wong-Stall, F. 1984. Molecular Characterization of Human T-cell Leukemia (lymphotropic) Virus Type III in the Acquired Immune Deficiency Syndrome. Science 226,1165–1171.

5. Popovic, M., Sarngadharan, M. G., Read, E., and Gallo, R. C. 1984. Detection, Isolation, and Continuous Production of Cytopathic Retroviruses (HTLV-III) From Patients with AIDS and pre-AIDS. Science 224,497–500.

6. Harada, S., Koyanagi, Y. and Yamamoto, N. 1985. Infection of the Human T-lymphotropic Virus Type-I (HTLV-I)-Bearing MT-4 Cells With HTLV-III (AIDS virus): Chronological Studies of Early Events. Virology 146,272,281.

7. Sundstrom, C. and Nilsson, K. 1976. Establishment and Characterization of a Human Histiocytic Lymphoma Cell Line (U937). Int. J. Cancer 17,565–577.

8. Poiesz, B. J., Ruscetti, F.W., Gazdar, A. F., Bunn, P. A., Minna, J. D., and Gallo, R. C. 1980. Detection and Isolation of Type C Retrovirus Particles From Fresh and Cultured Lymphocytes of a Patient With Cutaneous T-cell Lymphoma. Proc. Natl. Acad. Sci. (U.S.A.) 77,7415–7419.

9. Montefiori, D. C. and Mitchell, W. M. 1987. Antiviral Activity of Mismatched double-stranded RNA Against Human Immunodeficiency Virus In Vitro. Proc. Natl. Acad. Sci. (U.S.A.) 84,2985–2989.

What is claimed is:

1. A method of protecting an animal or animal cells susceptible to human retroviral infection against viral-induced pathology secondary to antigenic drift, as evidenced by molecular rearrangement in the viral particle structure, comprising exposing the animal or cells isolated from the animal to a mismatched dsRNA which is a complex of a polyinosinate and a polycytidylate containing from 1 in 5 to 2 in 30 uracil or guanadine bases, or $rI_n \cdot r(C_{29},G)_n$ or $rI_n \cdot r(C_{11-14},U)_n$.

2. A method of stabilizing the molecular arrangement of a human retroviral particle structure and maintaining the particle's molecular arrangement within predetermined limits, comprising exposing the virus, or animal cells containing the virus, to a mismatched dsRNA in an amount and for a period of time sufficient to maintain the molecular arrangement of the viral particle structure within said limits, wherein the mismatched dsRNA is a complex of a polyinosinate and a polycytidylate containing from 1 in 5 to 2 in 30 uracil or guanadine bases, or $rI_n \cdot r(C_{29},G)_n$ or $rIn \cdot r(C_{11-14},U)_n$, or a dsRNA that contains regions of bond breakage and exhibits the favorable therapeutic ratio property of $rI_n \cdot r(C_{11-14},U)_n$.

3. A method of reducing the effects of antibody-dependent viral enhancing factors in a host infected with a human retrovirus and promoting the host's immune system to raise antibodies against the human retrovirus, comprising administering to the host an effective amount of a mismatched dsRNA which is a complex of a polyinosinate and a polycytidylate containing from 1 in 5 to 2 in 30 uracil or guanadine bases, or $rI_n \cdot r(C_{29},G)_n$ or $rI_n \cdot r(C_{11-14}, U)_n$, or a dsRNA that contains regions of bond breakage and exhibits the favorable therapeutic ratio property of $rI_n \cdot r(C_{11-14}, U)_n$.

4. A method of stabilizing the genomic content of a human retroviral particle comprising administering, to a host infected with a human retrovirus, or animal cells containing a human retrovirus, a mismatched dsRNA which is a complex of a polyinosinate and a polycytidylate containing from 1 in 5 to 2 in 30 uracil or guanadine bases, or $rI_n \cdot r(C_{29},G)_n$ or $rI_n \cdot r(C_{11-14},U)_n$, or a dsRNA that contains regions of bond breakage and exhibits the favorable therapeutic ratio property of $rI_n \cdot r(C_{11-14},U)_n$ wherein the amount of dsRNA administered is sufficient to stabilize the genomic content of the human retroviral particle.

5. The method of claim 4, in which the human retroviral particle is human immunodeficiency virus.

6. The method of claim 5, in which the envelope gene of the human immunodeficiency virus is stabilized.

7. The method of claim 2 or 4, in which the virus is contained in animal cells.

8. The method of claim 1, 2, 3 or 4, in which the mismatched dsRNA is a complex of a polyinosinate and a polycytidylate containing from 1 in 5 to 1 in 30 uracil or guanadine bases.

9. The method of claim 1, 2, 3 or 4, in which the mismatched dsRNA is $rI_n \cdot r(C_{29},G)_n$.

10. The method of claim 1, 2, 3 or 4, in which the mismatched dsRNA is $rI_n \cdot r(C_{11-14},U)_n$.

11. The method of claim 1, 2, 3 or 4, in which the dsRNA contains regions of bond breakage and the dsRNA exhibits the favorable therapeutic ratio property of $rI_n \cdot r(C_{11-14},U)_n$.

* * * * *